United States Patent
Thomas, III et al.

(12)

(10) Patent No.: US 10,675,362 B2
(45) Date of Patent: Jun. 9, 2020

(54) PHOTOLUMINESCENT NANOPARTICLES AND THEIR USES IN DETECTION OR QUANTIFICATION OF SINGLET OXYGEN

(71) Applicant: Trustees of Tufts College, Medford, MA (US)

(72) Inventors: Samuel W. Thomas, III, Middleton, MA (US); Fanny Frausto, Somerville, MA (US); Jingjing Zhang, Willowbrook, IL (US)

(73) Assignee: Trustees of Tufts College, Medford, MA (US)

( * ) Notice: Subject to any disclaimer, the term of this patent is extended or adjusted under 35 U.S.C. 154(b) by 0 days.

(21) Appl. No.: 15/665,902

(22) Filed: Aug. 1, 2017

(65) Prior Publication Data

US 2018/0036434 A1    Feb. 8, 2018

Related U.S. Application Data

(60) Provisional application No. 62/369,906, filed on Aug. 2, 2016.

(51) Int. Cl.
| | | |
|---|---|---|
| *A61K 49/00* | (2006.01) | |
| *G01N 33/58* | (2006.01) | |
| *G01N 33/84* | (2006.01) | |
| *A61K 47/64* | (2017.01) | |
| *G01N 33/542* | (2006.01) | |
| *A61K 41/00* | (2020.01) | |

(52) U.S. Cl.
CPC ...... *A61K 49/0021* (2013.01); *A61K 41/0057* (2013.01); *A61K 47/64* (2017.08); *A61K 49/0093* (2013.01); *G01N 33/542* (2013.01); *G01N 33/582* (2013.01); *G01N 33/587* (2013.01); *G01N 33/84* (2013.01)

(58) Field of Classification Search
CPC .............................. A61K 49/00; G01N 33/58
See application file for complete search history.

(56) References Cited

U.S. PATENT DOCUMENTS

| | | | | |
|---|---|---|---|---|
| 2002/0127224 A1* | 9/2002 | Chen | ...................... | A61K 39/44 424/130.1 |
| 2007/0249087 A1* | 10/2007 | Zhu | ........................ | B82Y 10/00 438/99 |
| 2018/0036408 A1* | 2/2018 | Bourke | ................ | A61K 41/008 |

OTHER PUBLICATIONS

Thomas III et al., Chem. Rev. 2007, 107, 1339-1386.*

* cited by examiner

*Primary Examiner* — Zohreh A Fay
(74) *Attorney, Agent, or Firm* — Occhiuti & Rohlicek LLP

(57) ABSTRACT

A composition, as well as methods using the composition, for detection or quantification of a molecule at a singlet state (e.g., singlet oxygen). The composition includes one or more nanoparticles, and the nanoparticle has an energy donor, an energy acceptor associated with the energy donor, and an energy transfer mechanism between the energy donor and the energy acceptor.

17 Claims, 9 Drawing Sheets

PHOTOLUMINESCENT NANOPARTICLES AND THEIR USES IN DETECTION OR QUANTIFICATION OF SINGLET OXYGEN

CROSS-REFERENCE TO RELATED APPLICATIONS

This application claims the benefit of U.S. provisional patent application No. 62/369,906 filed Aug. 2, 2016, the disclosure of which is herewith incorporated by reference in its entirety.

STATEMENT REGARDING FEDERALLY FUNDED RESEARCH

This invention was made with government support under CHE-1305832 awarded by the National Science Foundation. The government has certain rights in the invention.

FIELD OF INVENTION

The present invention relates to nanoparticles, and more specifically, to photoluminescent nanoparticles that are responsive to singlet oxygen.

BACKGROUND

Singlet oxygen ($^1O_2$) is a cytotoxic reactive oxygen species that can play a key role in photodynamic therapy and a variety of important processes in plants. Singlet oxygen can also be used as a secondary analyte in biological assays (e.g., the Alpha technology from PerkinElmer). Thus, researches have focused on detection and quantification of singlet oxygen in vitro and in vivo.

Fluorescent probes showing response to singlet oxygen have been used in the detection or quantification of singlet oxygen. However, currently available fluorescent probes suffer from major drawbacks, such as being not suitable for in vivo applications (e.g., intracellular imaging).

SUMMARY

In one aspect, the invention includes a composition for use in detection or quantification of a molecule at a singlet state. Such composition includes a nanoparticle having an energy donor, an energy acceptor having an acceptor ground state and an acceptor excited state, the energy acceptor being associated with the energy donor, and an energy transfer mechanism between the energy donor and energy acceptor. In the presence of the molecule at the singlet state, the energy acceptor reacts with the molecule to reduce a degree of energy transfer on the energy transfer mechanism and reduce an emission of a first radiation associated with a conversion of the energy acceptor from the acceptor excited state to the acceptor ground state.

In some embodiments, the molecule at the singlet state is singlet oxygen ($^1O_2$). The energy acceptor can be complexed with the energy donor by one or more non-covalent interactions. Alternatively, the energy acceptor can be linked with the energy donor by one or more covalent bonds. The energy transfer mechanism can be a Fluorescence Resonance Energy Transfer (FRET) or an electron exchange energy transfer.

In some embodiments, the energy donor has a donor ground state and a donor excited state, and a conversion of the energy donor from the donor ground state to the donor excited state is associated with an absorption of a second radiation (e.g., light) by the energy donor. In certain embodiments, the energy donor at the donor excited state emits a third radiation. The energy donor can be a photoluminescent polymer that, at the donor excited state, emits light, e.g., the photoluminescent polymer at the donor excited state can emit light through fluorescence or phosphorescence. In certain embodiments, the photoluminescent polymer is a conjugated polymer, e.g., the photoluminescent polymer can be represented as

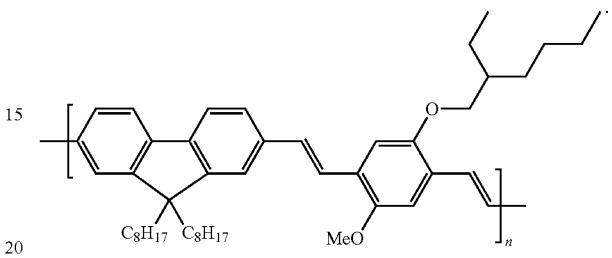

In some embodiments, the energy acceptor is converted from the acceptor ground state to the acceptor excited state upon receiving energy from the energy donor. The energy acceptor can be a luminescent molecule that, at the acceptor excited state, emits light, e.g., the luminescent molecule at the acceptor excited state can emit light through fluorescence or phosphorescence.

In certain embodiments, the luminescent molecule reacts with the singlet oxygen ($^1O_2$) to form a deactivated luminescent molecule and reduce the degree of the energy transfer mechanism. The luminescent molecule can include polycyclic aromatic hydrocarbons, e.g., an acene, helicene, phenancene, or a derivative thereof. The acene can be represented as

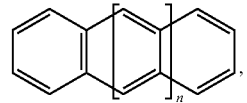

and n is 0, 1, 2, 3, 4, 5, 6, or 7. In certain embodiments, the derivative of the acene is a thiophene fused-acene, e.g., a thiophene fused-tetracene. For example, the luminescent molecule can be represented as

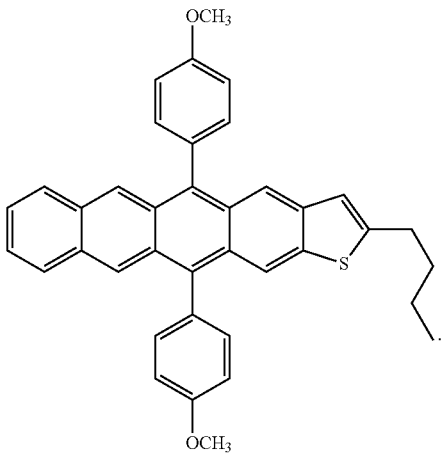 [SMILES: CCCCc1cc2cc3c(-c4ccc(OC)cc4)c4cc5ccccc5cc4c(-c4ccc(OC)cc4)c3cc2s1]

In another respect, the invention includes a method for detection or quantification of a molecule of a singlet state in a subject. The method includes administering to the subject a nanoparticle including an energy donor, an energy acceptor having an acceptor ground state and an acceptor excited state, the energy acceptor being associated with the energy donor, and an energy transfer mechanism between the energy donor and energy acceptor. In the presence of the molecule at the singlet state, the energy acceptor reacts with the molecule to reduce a degree of energy transfer on the energy transfer mechanism and reduce an emission of a first radiation associated with a conversion of the energy acceptor from the acceptor excited state to the acceptor ground state. The method further includes introducing a second radiation to the nanoparticle and measuring, at a first time point, the intensity of light emitted by the nanoparticle at one or more wavelengths.

In some embodiments, the method further includes measuring, at a second time point later than the first time point, the intensity of light emitted by the nanoparticle at the one or more wavelengths, and determining the amount of the molecules of the singlet state that react with the energy acceptor between the first and second time points.

The molecule at the singlet state can be singlet oxygen ($^1O_2$). The subject can be an animal, e.g., a human. The human can contain tumor cells and/or singlet oxygen. The subject can also be a sample, e.g., a bioassay sample. The sample can contain singlet oxygen.

In another respect, the invention includes a method for treating a medical condition in a subject. The method includes administering to the subject a nanoparticle including an energy donor, an energy acceptor having an acceptor ground state and an acceptor excited state, the energy acceptor being associated with the energy donor, and an energy transfer mechanism between the energy donor and energy acceptor. In the presence of the molecule at the singlet state, the energy acceptor reacts with the molecule to reduce a degree of energy transfer on the energy transfer mechanism and reduce an emission of a first radiation associated with a conversion of the energy acceptor from the acceptor excited state to the acceptor ground state. The method also includes introducing a second radiation to the nanoparticle, and detecting or measuring the light emitted by the nanoparticle at one or more wavelengths.

By reciting "detect", "detecting", or "detection", we refer to determining the presence of a target (e.g., singlet oxygen) to the extent that the amount of the target is above the lower detectable limit of the technique or instrument used.

By reciting "quantify", "quantifying", or "quantification", we refer to determining the amount of a target (e.g., singlet oxygen) to the extent that the amount of the target is above the lower detectable limit of the technique or instrument used.

By reciting "singlet state", we refer to an electronic state that a molecule or a portion thereof is at such that all electron spins in the molecule or the portion thereof are paired.

By reciting "ground state", we refer to an energy state that an element (e.g., energy donor or energy acceptor) resides at before absorption of energy (e.g., by radiation or by energy transfer). We can also refer to an energy state that the element resides at after emission of energy (e.g., by radiation or by energy transfer).

By reciting "excited state", we refer to any energy state greater than the ground state of an element. The element can reside at an excited state after absorption of energy (e.g., by radiation or by energy transfer) or before emission of energy (e.g., by radiation or by energy transfer).

By reciting "complex", "complexing", or "complexed", we refer to a state in which two or more elements (e.g., energy donor and energy acceptor) are associated by one or more non-covalent interactions. The interaction can exist between the two or more elements (e.g., an attractive force) or exist between another element and at least one of the two or more elements (e.g., a repulsive force).

By reciting "deactivate", "deactivating", "deactivated", or "deactivation", we refer to a state in which an element (e.g., energy acceptor) does not, or does substantially less, perform or enable at least one functions that the element performs or enables in another state. We can also refer to the function that is impaired or inhibited when the element resides at the state.

DETAILED DESCRIPTION

Figure 1:
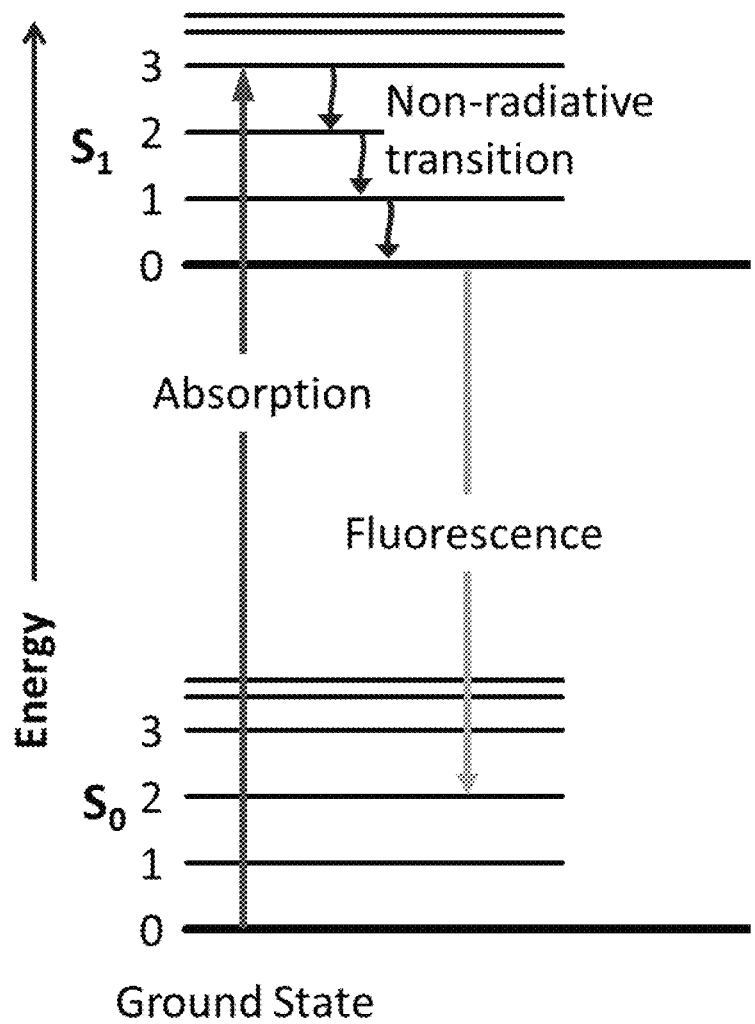
FIG. 1 is an energy diagram illustrating the mechanism of fluorescence.

Photoluminescence is light emission after the absorption of electromagnetic radiation (i.e., photon). Fluorescence is a form of photoluminescence that the emission of light is by a particular mechanism. As shown in FIG. 1, upon absorption of a photon, a system is excited electronically and vibrationally from its ground state ($S_0$) to an excited state (Si). The system then relaxes vibrationally between excited states, and eventually, the system relaxes from the excited state (Si) to the ground state ($S_0$) and emits light at a longer wavelength (fluoresces).

In most cases of fluorescence, the emitted light has a longer wavelength than the absorbed radiation. This feature allows fluorescence to be used in developing various analytical methods in chemistry and biology.

Figure 2:
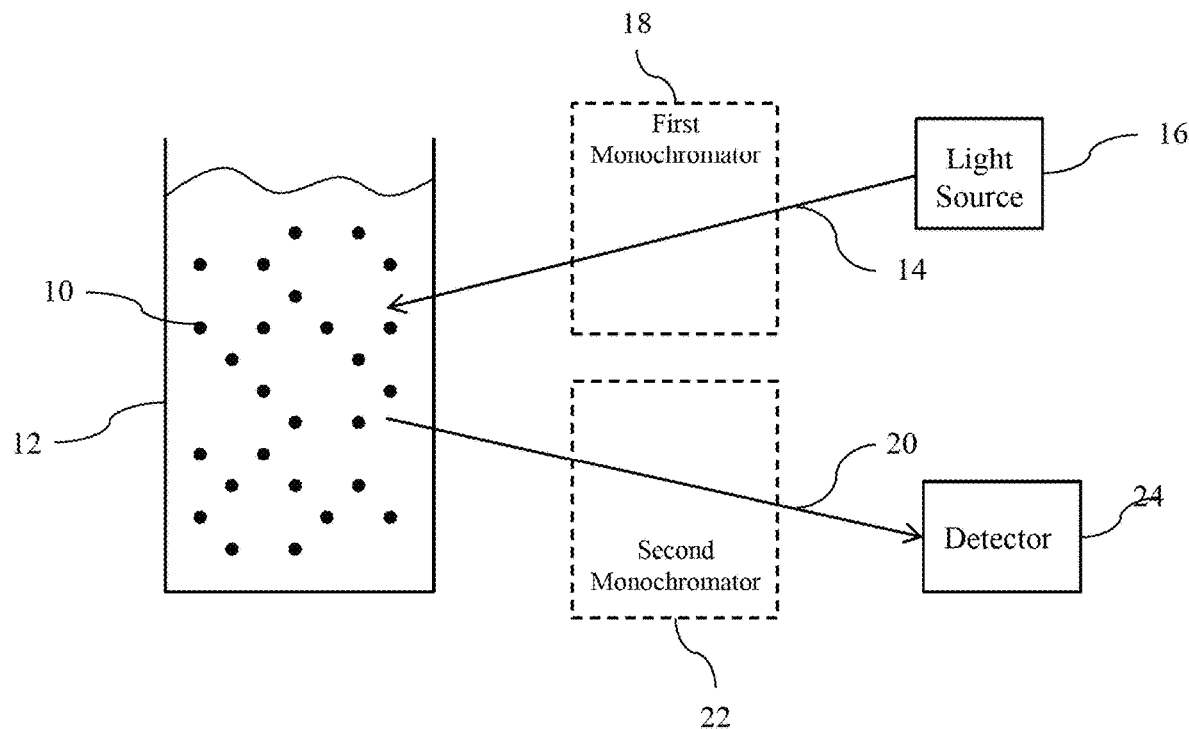
FIG. 2 illustrates a fluorescent probe used for detecting or quantifying singlet oxygen in a sample cell.

Referring to FIG. 2, a fluorescent probe 10 is used for detecting or quantifying singlet oxygen in a sample cell 12. An excitation light 14, produced by a light source 16, is filtered at one or more chosen wavelengths (e.g., by a first monochromator 18) and then passes through the sample cell. After absorption of the filtered excitation light, probe 10 emits light 20 by fluorescence. The emitted light 20 may be filtered at one or more wavelengths (e.g., by a second monochromator 22) and is then be observed and/or measured by a detector 24.

Currently, methods for detecting or quantifying singlet oxygen involve using a fluorescent probe (e.g., a molecule or an enzyme) that is reactive to singlet oxygen. These probes are often based on a fluorescence quenching mechanism that alternates between the absence and presence of singlet oxygen.

Figure 3:
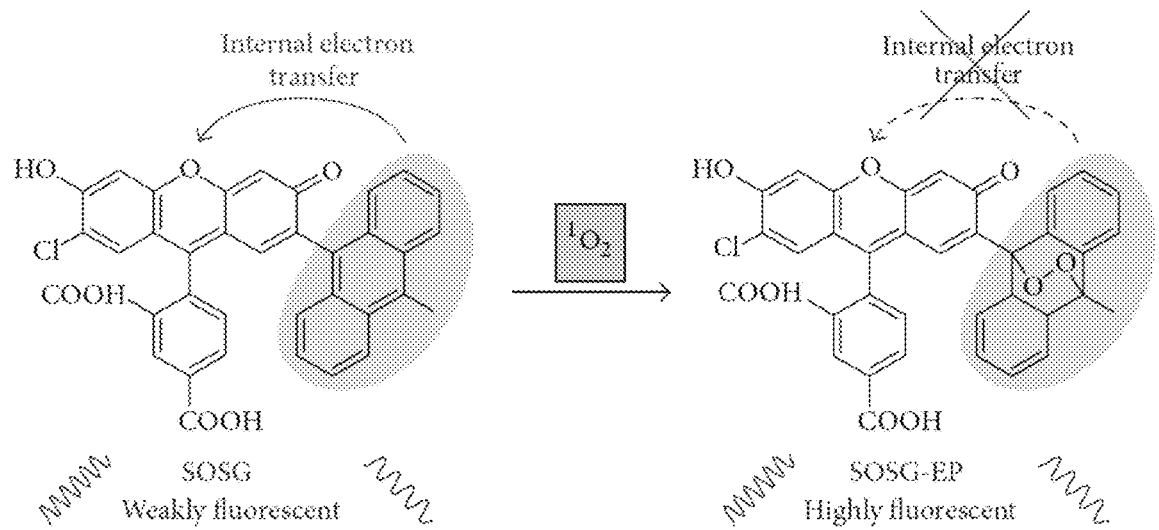
FIG. 3 illustrates the structure and working mechanism of Single Oxygen Sensor Green.

Referring to FIG. 3, Single Oxygen Sensor Green (SOSG) includes an anthracene moiety that may be excited upon absorption of a photon and an internal electron transfer mechanism that quenches the fluorescence from the anthracene moiety. Thus, in the absence of singlet oxygen, only weak fluorescent signals are observed. In the presence of singlet oxygen, however, the anthracene moiety reacts with the singlet oxygen to form an endoperoxide, and the internal electron transfer mechanism is inhibited. Thus, a strong fluorescent signal is observed.

Generally, the intensity of the emission light increases at all observed wavelengths in the presence of singlet oxygen. Thus, using such probes, the level of singlet oxygen can only be derived from the florescence lifetime of the probe. In order to measure the level of singlet oxygen directly, specialized techniques, such as a pulsed light source or a time-resolved detection system, are often required.

Alternatively, ratiometric methods allow measurement of the level of singlet oxygen without requiring specialized techniques and often allow for correction of artifacts. Generally, these methods require a fluorescent probe such that, while the level of singlet oxygen increases, the emission light by the probe increases at one wavelength and decreases at another wavelength. New fluorescent probes enabling these methods can be valuable in photoactivated fluorescence for tracking and high-resolution nanoscopy, amplified production of singlet oxygen for use in bioassays, and intracellular imaging of singlet oxygen.

As discussed in greater detail below, compositions including nanoparticles having an energy donor and an energy acceptor that are responsive to a molecule at a singlet state (e.g., singlet oxygen) may enable ratiometric detection or quantification of the molecule.

Figure 4A:
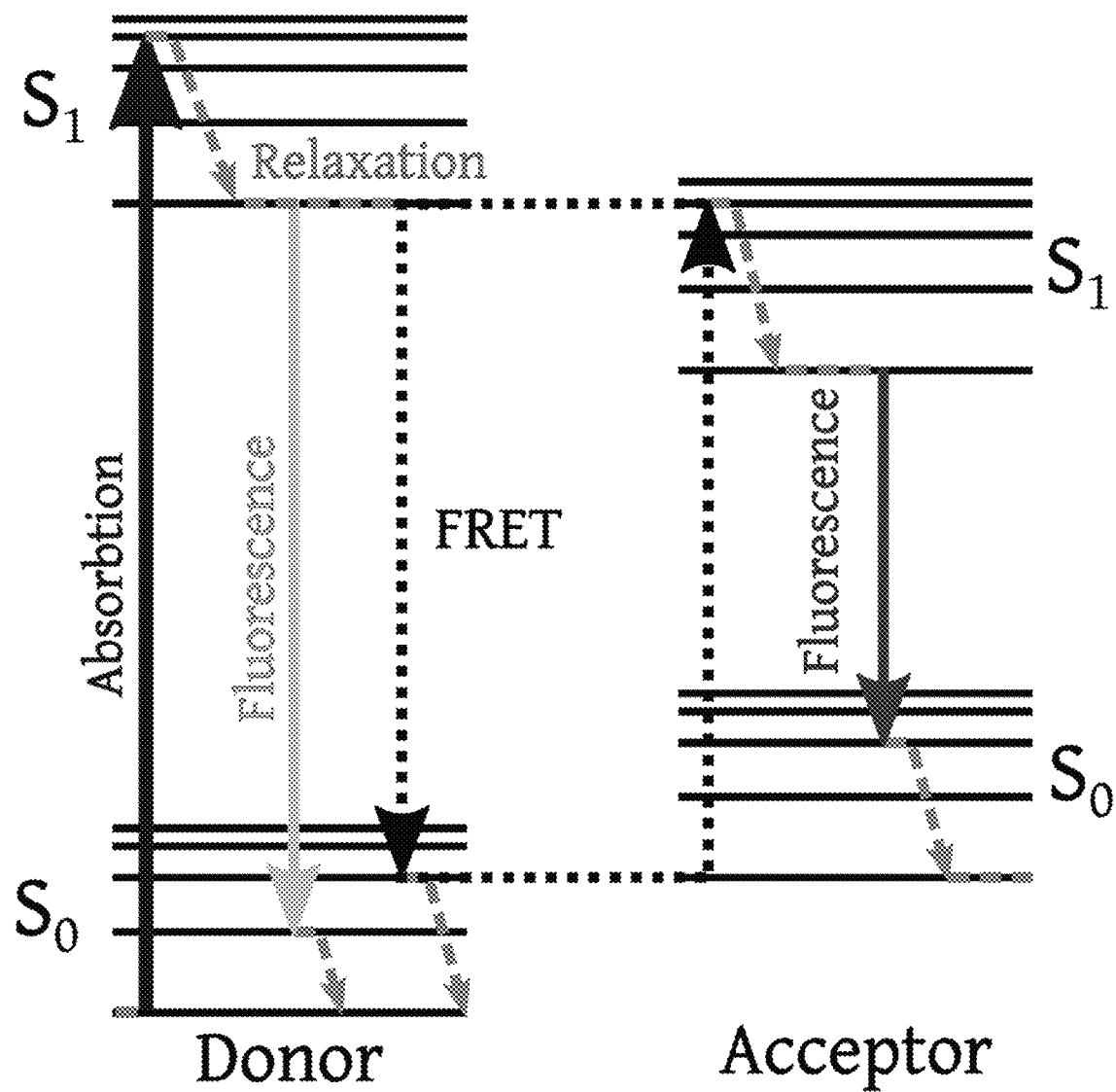
FIG. 4A is an energy diagram illustrating the working mechanism of one embodiment of the present invention.
Figure 4B:
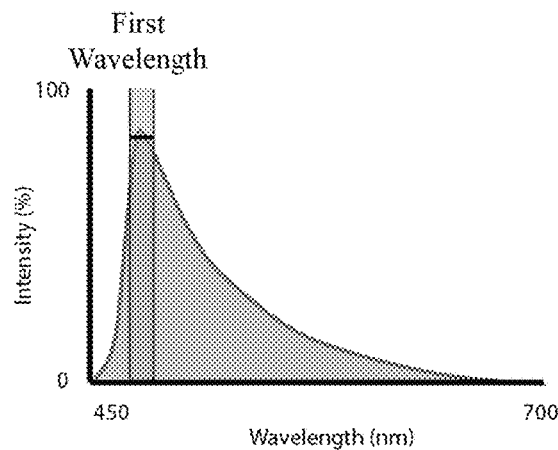
FIGS. 4B and 4C include fluorescence spectra of the light emitted by the energy donor and energy acceptor of the embodiment, respectively.
Figure 4C:
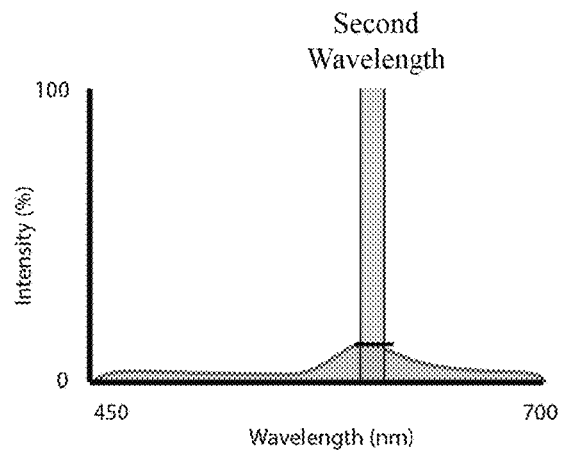
Figure 4D:
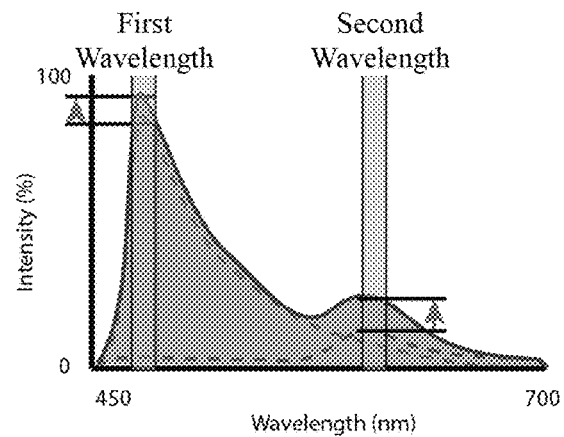
FIGS. 4D and 4E show fluorescence spectra of the observed light at low level and high level of singlet oxygen, respectively.
Figure 4E:
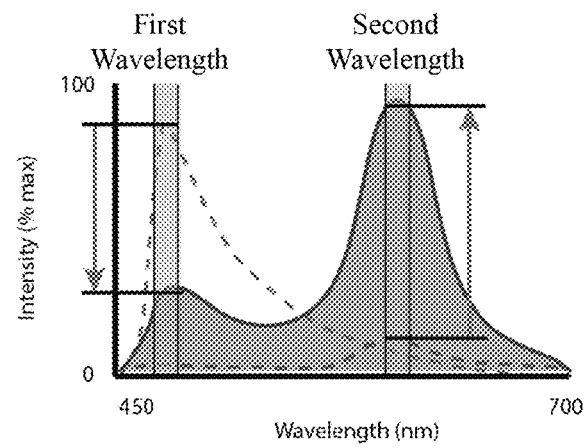

Referring to FIGS. 4A-4E, in an exemplary embodiment of a composition (described in greater detail below), an energy donor is configured to be excited upon absorption of a photon. While the excited energy donor is able to emit a first light (that is most intense at a first wavelength, shown in FIG. 4B) by fluorescence, the excited energy donor is also able to give energy to the energy acceptor by Fluorescence Resonance Energy Transfer (FRET). Upon receiving the energy, the energy acceptor is excited and then emits a second light (that is most intense at a second wavelength, shown in FIG. 4C) by fluorescence. In addition, the energy acceptor is configured to react with singlet oxygen to form a deactivated energy acceptor, and the FRET between the energy donor to the deactivated energy acceptor is inhibited. Thus, as the level of singlet oxygen increases, energy transfer by the FRET is reduced. As shown in FIGS. 4D and 4E, the intensity of the observed light (i.e., a combination of the first and second lights) increases at the first wavelength and decreases at the second wavelength. The level of singlet oxygen can then be determined based on the ratio between the intensities at the first and second wavelengths.

Detected and/or Quantified Molecules

The molecule to be detected or quantified by the composition described immediately above can be any molecule at a singlet state, i.e., the molecule or a portion thereof is at a molecular electronic state such that all electron spins are paired. In certain embodiments, the molecule can be singlet oxygen ($^1O_2$).

In certain embodiments, the singlet oxygen can be produced by various chemical methods. The singlet oxygen can be produced by photochemical methods, such as irradiating oxygen gas in the presence of an organic dye (e.g., rose bengal, methylene blue, or porphyrins). In other embodiments, the singlet oxygen can be produced by non-photochemical methods, such as decomposition of hydrogen trioxide, reaction of hydrogen peroxide with sodium hypochlorite, or decomposition of phosphate ozonide.

The singlet oxygen can also be produced in various biochemical or biological environments. In plants, the singlet oxygen can be produced in photosynthesis by light-harvesting molecules, such as chlorophyll (e.g., chlorophyll a, chlorophyll b, chlorophyll c1, chlorophyll c2, chlorophyll d, or chlorophyll) or other porphyrin pigments. In mammals, the generation of singlet oxygen can be associated with oxidation of LDL cholesterol and resultant cardiovascular effects. The singlet oxygen can also be produced inside or on the skin of animals (e.g., herbivorous animals, or human) that ingest the light-harvesting molecules (e.g., pigments capable of producing singlet oxygen with activation by light). Thus, the singlet oxygen can be associated with photosensitivity of skin (e.g., phototoxicity, photodermatitis, or phytophotodermatitis).

In some embodiments, the singlet oxygen can be produced in various therapeutic treatments, such as phototherapy (e.g., photodynamic therapy).

Nanoparticle

In some embodiments, the nanoparticle can be a particle having a size (e.g., diameter) from 1 to 100 nm. For examples, the nanoparticle can have a diameter from 1 to 10 nm (e.g., 1 nm, 2 nm, 3 nm, 4 nm, 5 nm, 6 nm, 7 nm, 8 nm, 9 nm, 10 nm, or therebetween), or the nanoparticle can have a diameter from 10 to 100 nm (e.g., 10 nm, 20 nm, 30 nm, 40 nm, 50 nm, 60 nm, 70 nm, 80 nm, 90 nm, 100 nm, or therebetween. The nanoparticle can have one or more morphology or can be amorphous. In some embodiments, the nanoparticle can have a spherical shape. In other embodiments, the nanoparticle can be sphere, rod, fiber, cup, or other shapes.

The nanoparticle can include various types of molecules and/or materials. The molecule can be an organic molecule, inorganic molecule, or a combination thereof. In certain embodiments, the material can be a polymeric material. The nanoparticle can include one or more biological macromolecules (e.g., nucleic acids, proteins, carbohydrates, polyphenols, lipids, or macrocycles).

In the nanoparticle, the energy acceptor can be associated with the energy donor by various means. In some embodiments, the energy acceptor is complexed with the energy donor by one or more non-covalent interactions. The non-covalent interaction can be an electrostatic interaction (e.g., an ionic interaction, a hydrogen bonding, or a halogen bonding), Van der Walls force (e.g., a dipole-dipole interaction, a dipole-induced dipole interaction, or an induced dipole-induced dipole interaction), π-effect (e.g., a π-π interaction, a cation-π interaction, or an anion-π interaction), hydrophobic effect, or a combination thereof.

In other embodiments, the energy acceptor is linked with the energy donor by one or more covalent bonds. The covalent bond can be σ-bond, π-bond, metal-to-metal bond, agostic interaction, bent bond, three-center two-electron bond, or a combination thereof. The energy acceptor can be linked with the energy donor by one or more linkages that include the covalent bond(s). For examples, the linkage can be ether, thioether, ester, thioester, amid, disulfide, hydrazone, or a derivative thereof.

The energy transfer mechanism of the nanoparticle can use various means to allow energy transfer between the energy donor and the energy acceptor. For example, the energy transfer mechanism can be a Fluorescence Resonance Energy Transfer (FRET). In another example, the energy transfer mechanism can be a Dexter Electron Transfer (electron exchange energy transfer). In other embodiments, the energy transfer mechanism can be Surface energy transfer (SET) or Time-resolved fluorescence energy transfer (TR-FRET).

Energy Donor

As described above, the energy donor of the nanoparticle can be configured to be converted from the donor ground state to the donor excited state upon absorption of the second radiation. In some embodiments, the energy donor can further be converted from the donor excited state to the donor ground state and emit a third radiation.

The second radiation and the third radiation can be any one of a variety of different types of radiations, including electromagnetic radiation (e.g., radio wave, ultraviolet light, visible light, infared light, x-ray, or gamma radiation), particle radiation (e.g., alpha radiation, beta radiation, or neutron radiation), acoustic radiation (e.g., ultrasound, sound, or seismic wave), or gravitational radiation. In certain embodiments, the electromagnetic radiation can be a light (e.g., visible light) at one or more wavelengths (e.g., 380 nm, 390 nm, 400 nm, 410 nm, 420 nm, 430 nm, 440 nm, 450 nm, 460 nm, 470 nm, 480 nm, 490 nm, 500 nm, 510 nm, 520 nm, 530 nm, 540 nm, 550 nm, 560 nm, 570 nm, 580 nm, 590 nm, 600 nm, 610 nm, 620 nm, 630 nm, 640 nm, 650 nm, 660 nm, 670 nm, 680 nm, 690 nm, 700 nm, 710 nm, 720 nm, 730 nm, 740 nm, 750 nm, or therebetween).

The energy donor can emit the third radiation through various mechanisms. For example, the energy donor can emit the third radiation through fluorescence or phosphorescence. In some embodiments, the energy donor can be a polymer. For example, the energy donor can be a photoluminescent polymer that emits a light upon absorption of an electromagnetic radiation. The photoluminescent polymer can also be a conjugated polymer. Various photoluminescent polymer suitable for the energy donor have been described in the literature, e.g., Thomas et al. ("Chemical sensors based on amplifying fluorescent conjugated polymers," *Chem. Rev.* 107:1339-1386, 2007).

The energy donor can also be a commercially available fluorescent polymer. For example, the energy donor can be PFPV Polymer (i.e., poly[(9,9-dioctyl-2,7-divinylenefluorenylene)-alt-co-{2-methoxy-5-(2-ethylhexyloxy)-1,4-phenylene}]; sold by American Dye Source Inc., catalog No. ADS108GE) that is represented as

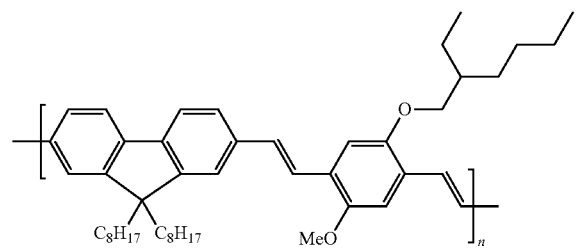

Other suitable polymers include poly(9-anthracenylmethyl acrylate), poly(9-anthracenylmethyl methacrylate), poly(3,3',4,4'-benzophenonetetracarboxylic dianhydride-alt-Acridine Yellow G), poly(3,3',4,4'-benzophenonetetracarboxylic dianhydride-alt-3,6-diaminoacridine hemisulfate), poly(ethylene oxide), poly(fluorescein O-acrylate), poly(fluorescein isothiocyanate allylamine hydrochloride) Poly (allylamine hydrochloride), poly(fluorescein O-methacrylate), poly[(4,4'-hexafluoroisopropylidene)diphthalic anhydride-alt-Acridine Yellow G], poly[(4,4'-hexafluoroisopropylidene)diphthalic anhydride-alt-3,6-diaminoacridine hemisulfate], poly[(methyl methacrylate)-co-(9-anthracenylmethyl methacrylate)], poly[methyl methacrylate-co-(fluorescein O-acrylate)], poly[(methyl methacrylate)-co-(fluorescein O-methacrylate)], poly[(methyl methacrylate)-co-(2-naphthyl methacrylate)], poly[(methyl methacrylate)-co-(N-(1-naphthyl)-N-phenylacrylamide)], poly[(methyl methacrylate)-co-(7-(4-trifluoromethyl)coumarin acrylamide)], poly[(methyl methacrylate)-co-(7-(4-trifluoromethyl) coumarin methacrylamide)], poly(2-naphthyl acrylate), poly (2-naphthyl methacrylate), poly[N-(1-naphthyl)-N-phenylacrylamide], poly[N-(1-naphthyl)-N-phenylmethacrylamide], poly(pyromellitic dianhydride-alt-acridine yellow G), poly(pyromellitic dianhydride-alt-3,6-diaminoacridine hemisulfate), poly(pyromellitic dianhydride-alt-ethidium bromide), poly(pyromellitic dianhydride-co-thionin), and poly(2-vinylnaphthalene).

Energy Acceptor

As described above, the energy acceptor of the nanoparticle can be configured such that energy transfer on the energy transfer mechanism can occur from the energy donor to the energy acceptor. Upon receiving energy, the energy acceptor is converted from the acceptor ground state to the acceptor excited state. The energy acceptor emits a first radiation upon conversion from the acceptor excited state to the acceptor ground state.

Like the energy donor described above, the first radiation can be any one of a variety of different types of radiations, including electromagnetic radiation (e.g., radio wave, ultraviolet light, visible light, infared light, x-ray, or gamma radiation), particle radiation (e.g., alpha radiation, beta radiation, or neutron radiation), acoustic radiation (e.g., ultrasound, sound, or seismic wave), or gravitational radiation. In certain embodiments, the first radiation can be a light (e.g., visible light) at one or more wavelengths (e.g., 380 nm, 390 nm, 400 nm, 410 nm, 420 nm, 430 nm, 440 nm, 450 nm, 460 nm, 470 nm, 480 nm, 490 nm, 500 nm, 510 nm, 520 nm, 530 nm, 540 nm, 550 nm, 560 nm, 570 nm, 580 nm, 590 nm, 600 nm, 610 nm, 620 nm, 630 nm, 640 nm, 650 nm, 660 nm, 670 nm, 680 nm, 690 nm, 700 nm, 710 nm, 720 nm, 730 nm, 740 nm, 750 nm, or therebetween). The energy acceptor can emit the first radiation through various mechanisms. For example, the energy donor can emit the first radiation through fluorescence or phosphorescence.

In certain embodiments, the energy acceptor is configured to react with the molecule at the singlet state (e.g., singlet oxygen) to reduce a degree of energy transfer on the energy transfer mechanism. This can be achieved by forming a deactivated energy acceptor (i.e., the energy transfer mechanism between the acceptor and the deactivated energy acceptor is impaired or inhibited). As the deactivated energy acceptor receives less or no energy from the energy donor, the emission of the first radiation can be reduced.

In some embodiments, the energy acceptor is a molecule, such as a luminescent molecule that, at the acceptor excited state, emits light. The luminescent molecule can include a moiety (e.g., allyl group, or 1,3-diene) that reacts with singlet oxygen.

In certain embodiments, the luminescent molecule can include polycyclic aromatic hydrocarbons constructed by two or more fused benzene rings. Acenes (or polyacenes) are a class of polycyclic aromatic hydrocarbons constructed by linearly fused benzene rings. In some embodiments, the luminescent molecule can include an acene or a derivative thereof. The acene can be represented as

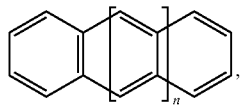

where n is 0 (naphthalene), 1 (anthracene), 2 (tetracene), 3 (pentacene), 4 (hexacene), 5 (heptacene), 6 (octacene), or 7 (nonacene). In preferred embodiments, the derivative of the acene can be a thiophene fused-acene (e.g., thiophene fused-tetracene). For example, the energy acceptor can be a molecule that is represented as

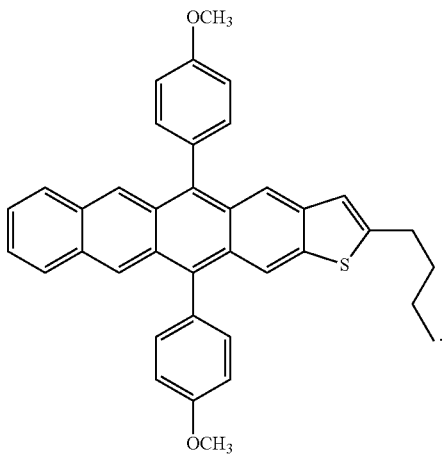 [SMILES: CCCCc1cc2cc3c(-c4ccc(OC)cc4)c4cc5ccccc5cc4c(-c4ccc(OC)cc4)c3cc2s1]

In other embodiments, the luminescent molecule can include other polycyclic aromatic hydrocarbons constructed by linearly or non-linearly fused benzene rings or derivatives thereof. For examples, the luminescent molecule can include helicene (e.g., [4]Helicene, [5]Helicene, [6]Helicene, [7]Helicene, [8]Helicene, [9]Helicene, [10]Helicene, [11]Helicene, [12]Helicene, [13]Helicene, [14]Helicene, [15]Helicene, [16]Helicene, [17]Helicene, or [18]Helicene) or phenancene (e.g., [4]phenacene, [5]phenacene, [6]phenacene, or [7]phenacene).

Detection and Quantification Methods

A method for detection or quantification of a molecule at a singlet state will now be described. The method can include administering to the subject any of the compositions described above, introducing a second radiation to the nanoparticle, and measuring, at a first time point, the intensity of light emitted by the nanoparticle at one or more wavelengths. The method can further include measuring, at a second time point later than the first time point, the intensity of light emitted by the nanoparticle at the one or more wavelengths. Based on the measured intensities, the amount of the molecules that react with the energy acceptor between the two time points can be determined.

In some embodiments, the subject can be a mammal (e.g., a human). The subject can also be a domesticated animal (e.g., a dog or cat). The subject can also be an animal kept as livestock (e.g., cattle, sheep, chickens, horses, pigs, or goats). The subject can also be a cell, tissue, organ, organ system, organism, or a medium containing one or more of these. In other embodiments, the subject can be a sample (e.g., a bioassay sample). In certain embodiments, the bioassay sample can include one or more proteins.

Various types of techniques can be used to detect or measure the emitted radiation (e.g., the first or third radiation) of the present invention. As a typical technique, spectroscopy can be used, such as UV/Vis spectroscopy, IR spectroscopy, atomic absorption spectroscopy, emission spectroscopy, photoluminescent spectroscopy, atomic emission spectroscopy, and other spectroscopy based on absorption or scattering. In certain embodiments, the spectroscopy can be fluorescence spectroscopy or phosphorescence spectroscopy.

Imaging and Treating Medical Conditions

A method for imaging or treating a medical condition in a subject will now be described. The method includes administering to the subject any of the compositions described above.

The subject can be a mammal (e.g., a human, dog, or cat). The subject can also be an animal kept as livestock (e.g., cattle, sheep, chickens, horses, pigs, or goats). The subject can also be a cell, tissue, organ, organ system, organism, or a medium containing one or more of these.

In certain embodiments, the treatment can be a phototherapy. The phototherapy can include administering to the subject (e.g., a patient) daylight or one or more specific wavelengths of light using polychromatic polarized light, lasers, light-emitting diodes, fluorescent lamps, dichroic lamps or full-spectrum light. The light can be administered for a prescribed amount of time and/or at a specific time of day.

The phototherapy can be used for treating a skin condition. The skin condition can be psoriasis, vitiligo, acne vulgaris, cancer, eczema, neonatal jaundice, atopic dermatitis, polymorphous light eruption, cutaneous T-cell lymphoma, lichen planus, or a wound. The phototherapy can be used for treating a condition associated with mood and/or sleeping. The condition can be a circadian rhythm disorder (CRSD). The CRSD can be a chronic CRSD (e.g., delayed sleep phase disorder) or a situational CRSD (e.g., jet lag). In some embodiments, the CRSD is associated with Parkinson's disease. The condition can also be a seasonal affective disorder or a non-seasonal depression.

In certain embodiments, the phototherapy is a photodynamic therapy (PDT, also known as photochemotherapy). The phototherapy can be used for treating various conditions (e.g., conditions associated with cancer or acne vulgaris). The photodynamic therapy can use light, one or more photosensitizing chemical substances (i.e., photosensitizers), and molecular oxygen. The wavelength of the light can be selected such that the light excites the photosensitizer to produce radicals and/or reactive oxygen species. In some embodiments, the photodynamic therapy generates singlet oxygen.

The phototherapy can further include administering (e.g., systemically or topically) to the subject the photosensitizers. The photosensitizer can be a porphyrin, a chlorophyll, a dye, or a derivative thereof. In certain embodiments, the photosensitizer is aminolevulinic acid (ALA), silicon phthalocyanine Pc 4, m-tetrahydroxyphenylchlorin (mTHPC), mono-L-aspartyl chlorin e6 (NPe6), allumera, photofrin, visudyne, levulan, foscan, metvix, hexvix, cysview, laserphyrin, antrin, photochlor, photosens, photrex, lumacan, cevira, visonac, BF-200 ALA, amphinex, azadipyrromethenes, 9-acetoxy-2,7,12,17-tetrakis-(β-methoxyethyl)-porphycene (ATMPn), zinc phthalocyanine, or naphthalocyanine (NC). The photosensitizer can also be expanded metallo-porphyrin, metallochlorin, bacteriochlorin, metallo-phthalocyanine, metallo-naphthocyaninesulfobenzo-porphyrazines (M-NSBP), or metallo-naphthalocyanine.

In certain embodiments, the conditions treated or imaged is associated with a cancer. The cancer can be an adrenal cancer, an anal cancer, a bile duct cancer, a bladder cancer, a bone cancer, a brain cancer, a breast cancer, a castleman disease, a cervical cancer, a colon/rectum cancer, an endometrial cancer, an esophagus cancer, an eye cancer, a gallbladder cancer, a gastrointestinal carcinoid tumors, a gastrointestinal stromal tumor (gist), a gestational trophoblastic disease, a hodgkin disease, a kaposi sarcoma, a kidney cancer, a laryngeal and hypopharyngeal cancer, a leukemia, a liver cancer, a lung cancer, a lymphoma, a malignant mesothelioma, a multiple myeloma, a myelodysplastic syndrome, a nasal cavity and paranasal sinus cancer, a nasopharyngeal cancer, a neuroblastoma, a non-hodgkin lymphoma, an oral cavity and oropharyngeal cancer, an osteosarcoma, an ovarian cancer, a pancreatic cancer, a penile cancer, a pituitary tumors, a prostate cancer, a retinoblastoma, a rhabdomyosarcoma, a salivary gland cancer, a sarcoma, a skin cancer, a small intestine cancer, a stomach cancer, a testicular cancer, a thymus cancer, a thyroid cancer, a uterine sarcoma, a vaginal cancer, a vulvar cancer, a waldenstrom macroglobulinemia, a wilms tumor, a melanoma, an adenoma, a carcinoma of solid tissue, a hypoxic tumor, a genitourinary cancer, a head and neck cancer, a nervous system cancer, a benign lesion, or a combination of one or more thereof.

EXAMPLES

Preparation of Nanoparticles

PFPV Polymer (Poly[(9,9-dioctyl-2,7-divinylenefluorenylene)-alt-co-{2-methoxy-5-(2-ethylhexyloxy)-1,4-phenylene}]; a product of American Dye Source Inc., catalog No. ADS108GE) and 10% TMT (diphenyl-tetracenemonothiophene, prepared according to Altinok et al., *Polym. Sci., Part A: Polym. Chem.* 54:2526-2535, 2016) by weight of PFPV polymer were added to tetrahydrofuran (THF) to form a solution with a total concentration of 1 mg/mL. The solution was then diluted to 0.2 mg/mL with THF, and 2 mL of the diluted solution was quickly added to 8 mL of Millipore water (purified by Milli-Q® systems from EMD Millipore) with ultrasonication. THF was removed from the mixture though rotary evaporation. A suspension containing the nanoparticles (F8MEHPPV TMT NP) was formed. The suspension is stable for 2 weeks and was used as is.

Testing Nanoparticles with Methylene Blue

Methylene blue (MB) is a known generator of singlet oxygen. Thus, we tested our nanoparticles in detection of singlet oxygen generated by methylene blue.

A sample of the nanoparticles in Millipore water with an optical density (OD) of 0.10 was prepared. To investigate the nanoparticles' reactivity towards singlet oxygen, a solution of methylene blue (MB) was added to the sample until the OD reaches 0.10 at MB's absorption peak. The sample was then irradiated with a filter at 630 nm to selectively irradiate MB to generate singlet oxygen through sensitization. The filtered irradiation limits the self-sensitization of the TMT moiety by the nanoparticles. The energy transfer (ET) between the donor (PFPV polymer) and the acceptor (TMT) was monitored through emission spectroscopy with excitation at the PFPV polymer's band. The ratio of the donor signal ($I_D$) to the sum of the donor and acceptor signals ($I_D+I_A$) was then calculated.

Figure 5:
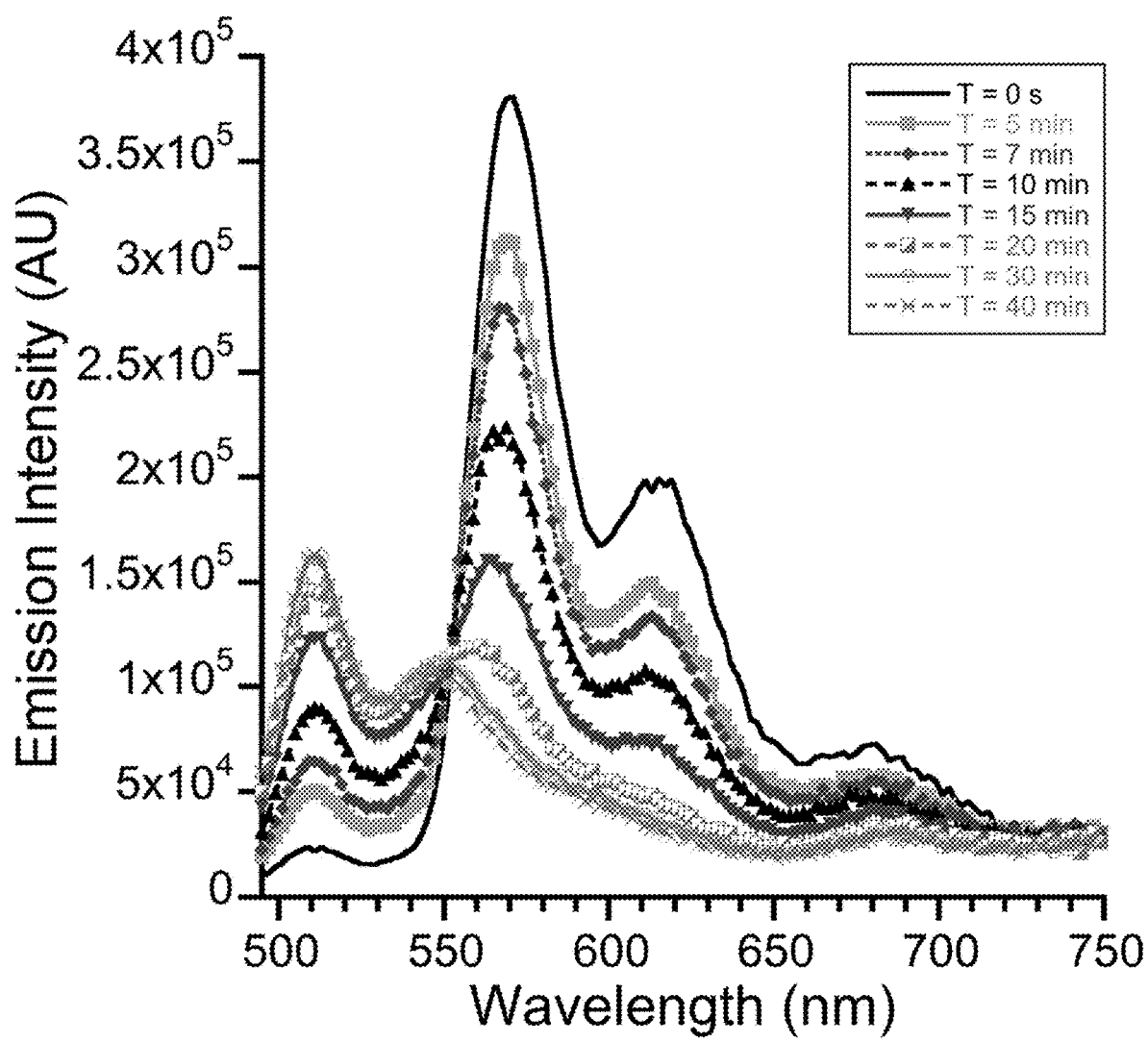
FIG. 5 is a fluorescence spectra of a mixture of nanoparticles (F8MEHPPV TMT NP) with methylene blue (MB) in $H_2O$.

As shown in FIG. 5, the acceptor signal ($I_A$) decreases with irradiation time of MB increases. This observation shows that, as singlet oxygen is being produced, TMT reacts in the singlet oxygen to form deactivated acceptor, and the energy transfer from the donor to the deactivated acceptor is inhibited. The emission spectra thus shift from primarily the acceptor signal to primarily the donor signal. The nanoparticles show a ratiometric response to singlet oxygen.

Figure 6:
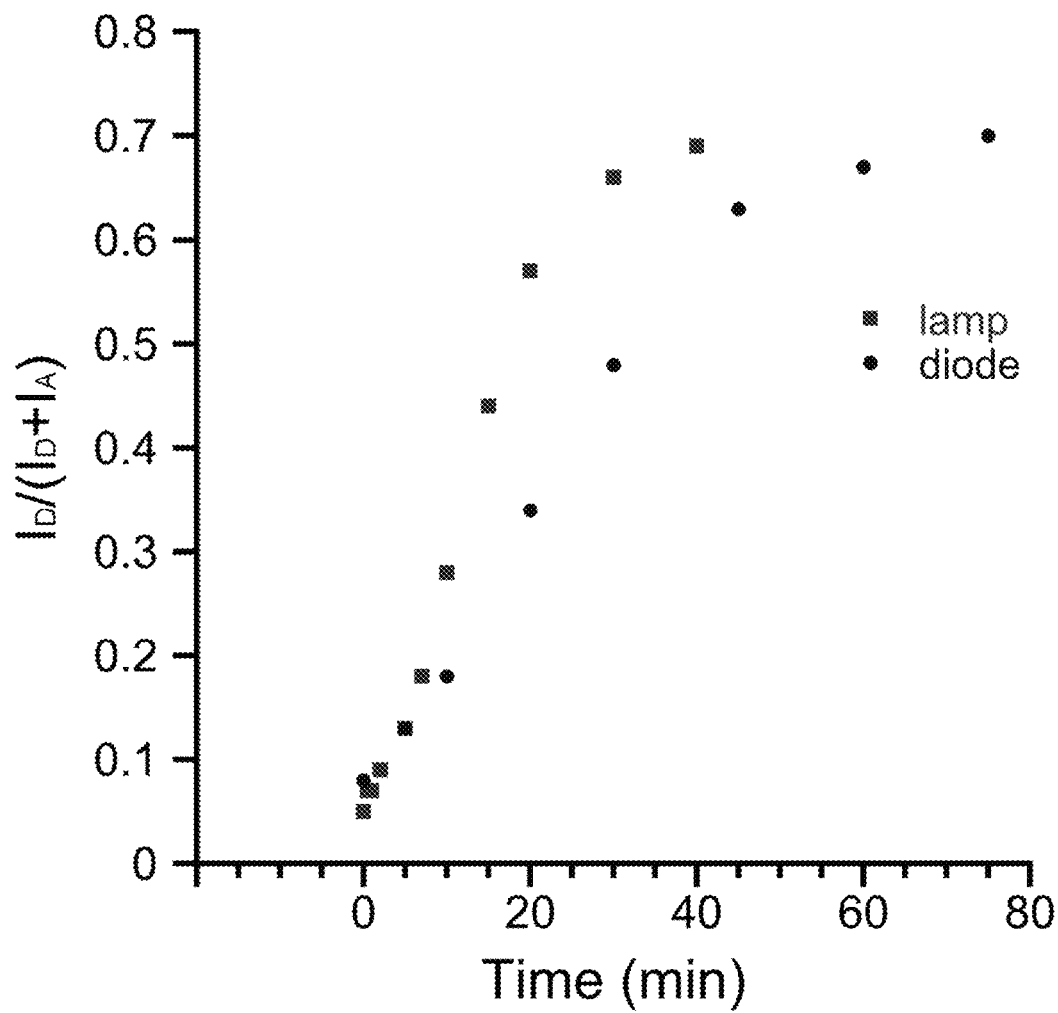
FIG. 6 is a graph comparing the use of a mercury lamp and a laser diode as an irradiation resource (at 635 nm).

Referring to FIG. 6, the system was tested with irradiation from two different resources: a mercury lamp and a laser diode. While the time to get an increase in signal is longer due to the lower power density provided by the resources, this increase corroborates that the TMT moiety is reacting at singlet oxygen generated by MB.

Testing Nanoparticles with Protein-Dye Conjugate

In order to probe the viability of the nanoparticles as a detecting unit in a sandwich immunoassay, we prepared a Protein-Dye conjugate that generates singlet oxygen upon irradiation. We chose Neutravidin (a product of Thermo Scientific Inc.) as the protein to limit non-specific binding and to take advantage of its strong biotin binding properties. We also chose a commercially available dye, IRDye 700 OX (bought from Licor), that generates singlet oxygen upon irradiation. IRDye 700 OX, as an N-hydroxysuccinimide (NHS) ester, was conjugated with Neutravidin using a commercial labeling kit. This Protein-Dye conjugate was kept in PBS buffer without preservatives.

Figure 7:
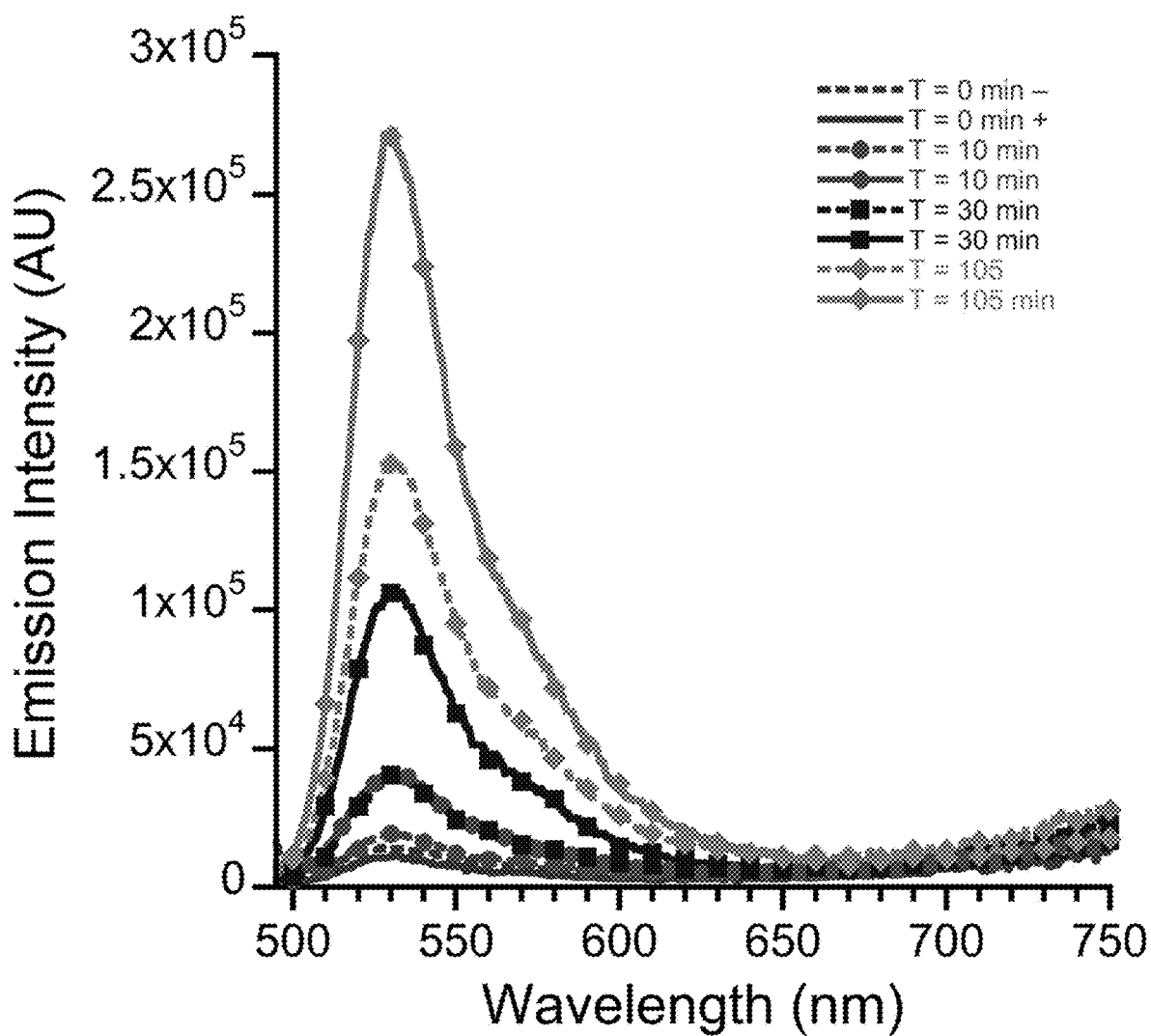
FIG. 7 is a fluorescence spectra comparing a mixture of Protein (Neutravidin) and SOSG (dashed lines) and a mixture of Protein-Dye conjugate (Neutravidin-IRDye 700 DX conjugate) and SOSG (solid lines).

To show that the Protein-Dye conjugate generates singlet oxygen upon irradiation, a commercially available sensor, singlet oxygen sensor green (SOSG), was used. As shown in FIG. 7, in a sample of Protein-Dye conjugate and SOSG (solid lines), the fluorescent signal of the SOSG increases as irradiation time increases, indicating the generation of singlet oxygen by the Protein-Dye conjugate. The result was further validated by a control experiment with a sample of Protein and SOSG (dashed lines).

Figure 8:
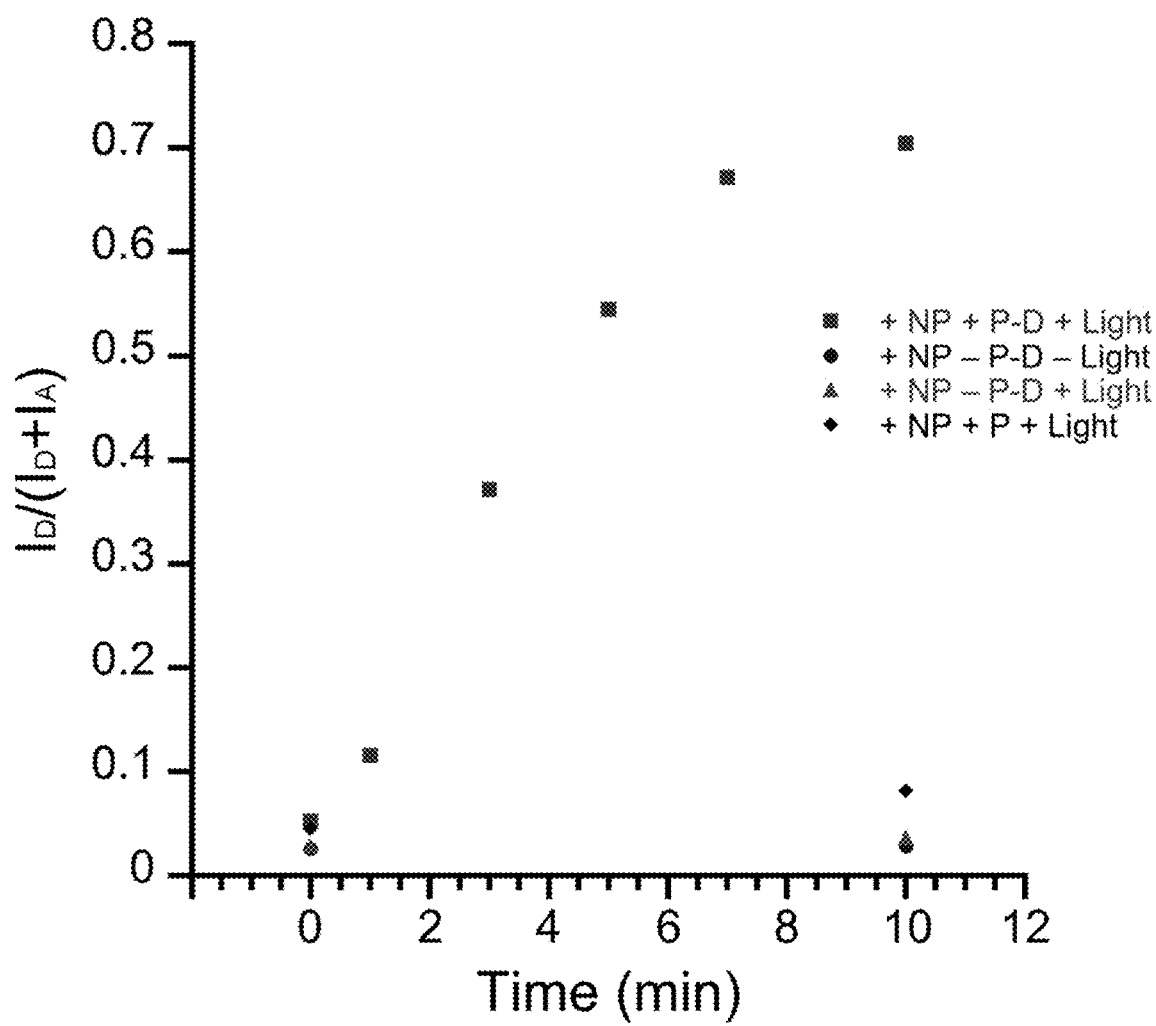
FIG. 8 is a graph comparing irradiation and control experiment of various samples containing nanoparticles (F8MEHPPV TMT NP).

We then tested the nanoparticle's response to singlet oxygen generated by the Protein-Dye conjugate. We prepared a sample of the nanoparticles and the Protein-Dye conjugate in Millipore water. FIG. 8 shows a comparison between irradiation and control experiment of various samples containing the nanoparticles. The boxes represent a sample of the nanoparticles and the Protein-Dye conjugate at OD of 1.00 irradiated with cut-on filters at 630 nm and 675 nm. The circles represent a sample of the nanoparticles at OD of 1.00 without irradiation. The triangles represent a sample of the nanoparticles at OD of 1.00 irradiated with cut-on filters at 630 nm and 675 nm. The diamonds represent a sample of the nanoparticles with Protein (at a similar concentration of protein used in the experiment represented by the boxes) irradiated with cut-on filters at 630 nm and 675 nm.

As shown in FIG. 8, the nanoparticles show very high reactivity to singlet oxygen upon irradiation. Further, limiting the exposure of these nanoparticles to any extraneous light made the probe highly sensitive to singlet oxygen only by reducing the background noise. This was achieved through irradiating the samples with two different cut-on filters in tandem, one at 630 nm and another at 675 nm. The filtration reduces the power density of the irradiation and limits the light at other wavelengths that causes self-sensitization, providing a lowered background noise and making this system a highly sensitive ratiometric probe of singlet oxygen in water.

Figure 9:
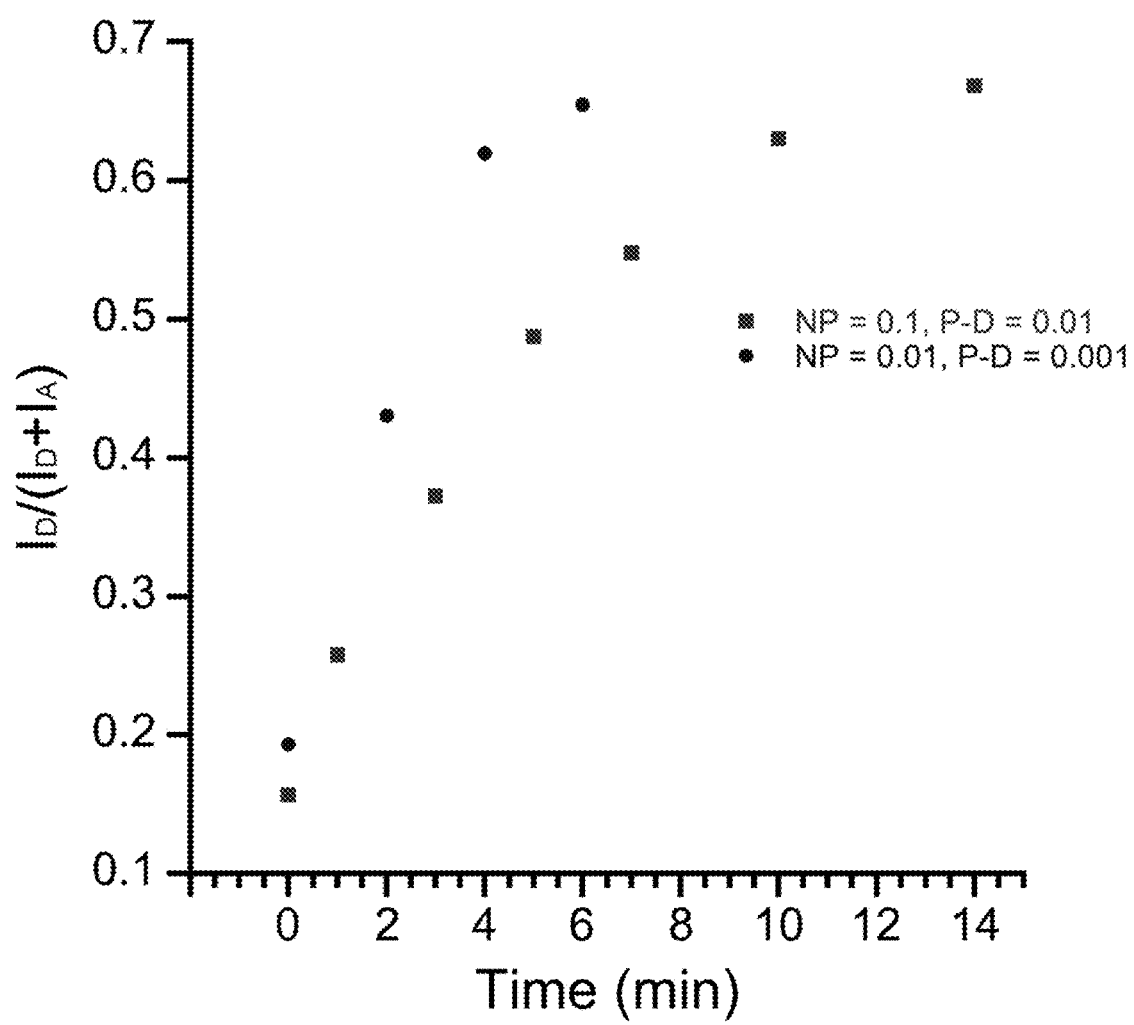
FIG. 9 is a graph illustrating comparison between irradiation of samples containing the nanoparticles and the Protein-Dye conjugate at lower concentrations.

As shown in FIG. 9, the sensitivity of the nanoparticles was further investigated. Samples with lower concentrations of the nanoparticles and the Protein-Dye conjugate were irradiated. We used a mercury lamp as the irradiation resource, and we filtered the irradiation at 630 nm and 675 nm. An increase in the donor signal ($I_D$) over irradiation time is observed, demonstrating that, even at low concentrations of the nanoparticles and the Protein-Dye conjugate, singlet oxygen is being produced and measured by the system.

What is claimed is:

1. A composition for use in detection or quantification of a molecule in a singlet state, wherein said composition comprises a nanoparticle, wherein said nanoparticle includes an energy donor, an energy acceptor, and an energy-transfer mechanism between said energy donor and said energy acceptor, wherein said energy acceptor has an acceptor ground-state and an acceptor excited-state, wherein the energy acceptor is associated with the energy donor, and wherein, in the presence of the molecule in the singlet state, the energy acceptor reacts with the molecule in the singlet state to reduce a degree of energy transfer on the energy-transfer mechanism and to reduce emission of first radiation associated with conversion of the energy acceptor from the acceptor excited-state to the acceptor ground-state, wherein the molecule that is in the singlet state is singlet oxygen, wherein the energy donor is a photoluminescent polymer that emits light in the course of undergoing a transition from an excited state thereof and wherein the energy acceptor comprises an acene.

2. The composition of claim 1, wherein the energy acceptor is complexed with the energy donor by at least one non-covalent interaction.

3. The composition of claim 1, wherein the energy acceptor is linked with the energy donor by at least one covalent bond.

4. The composition of claim 1, wherein the energy-transfer mechanism is Fluorescence Resonance Energy Transfer (FRET).

5. The composition of claim 1, wherein the energy-transfer mechanism is an electron exchange energy transfer.

6. The composition of claim 1, wherein the energy donor has a donor ground state and a donor excited state and wherein conversion of the energy donor from the donor ground state to the donor excited state is associated with absorption of second radiation by the energy donor.

7. A method for detection or quantification of a molecule that is in a singlet state in a subject, said method comprising administering a nanoparticle to said subject, exposing said nanoparticle to first radiation, measuring, at a first time, light intensity emitted by said nanoparticle in at least one wavelength, exposing the nanoparticle to second radiation, and measuring, at a first time, the intensity of light emitted by the nanoparticle at one or more wavelengths, wherein said nanoparticle comprises an energy donor, an energy acceptor, and an energy-transfer mechanism between said energy donor and said energy acceptor, wherein the molecule that is in the singlet state is singlet oxygen, wherein the energy donor is a photoluminescent polymer that emits light in the course of undergoing a transition from an excited state thereof, wherein the energy acceptor comprises an acene, wherein said energy acceptor has an acceptor ground-state and an acceptor excited-state, wherein the energy acceptor is associated with the energy donor, wherein, in the presence of the molecule in the singlet state, the energy acceptor reacts with the molecule to reduce a degree of energy transfer on the energy-transfer mechanism and to reduce emission of first and second radiation, and wherein the second radiation is associated with conversion of the energy acceptor from the acceptor excited-state to the acceptor ground-state.

8. The method of claim 7, wherein the method further comprises, at a second time later than the first time, measuring the intensity of light emitted by the nanoparticle at the one or more wavelengths and determining how many molecules of the singlet state reacted with the energy acceptor between the first time and a second time that is later than the first time, wherein measuring light intensity occurs at the second time.

9. The method of claim 7, wherein the subject is a human containing tumor cells or singlet oxygen.

10. The method of claim 9, wherein the subject is a bioassay sample.

11. The composition of claim 1, wherein said energy acceptor is thiophene fused-tetracene and wherein said thiophene fused-tetracene is converted from a ground state to an excited state thereof upon receiving energy from said energy donor.

12. The composition of claim 1, wherein said energy acceptor is converted from a ground state to an excited state thereof upon receiving energy from said energy donor, and wherein said energy acceptor, at said acceptor excited-state, emits light.

13. The composition of claim 1, wherein said energy acceptor is a thiophene fused-acene and wherein said thiophene fused-acene is converted from a ground state to an excited state thereof upon receiving energy from said energy donor.

14. The composition of claim 1, wherein said energy acceptor is converted from a ground state to an excited state thereof upon receiving energy from said energy donor, and wherein said energy acceptor is represented as

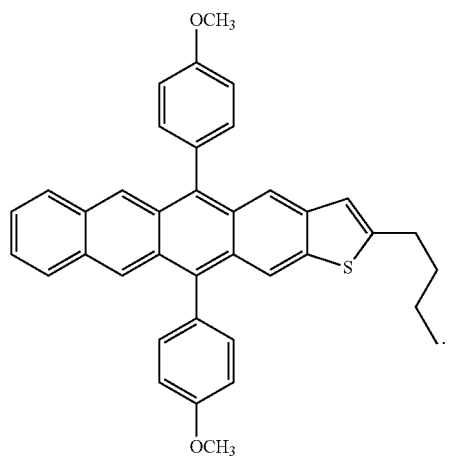 [SMILES: CCCCc1cc2cc3c(-c4ccc(OC)cc4)c4cc5ccccc5cc4c(-c4ccc(OC)cc4)c3cc2s1]

15. The composition of claim 1, wherein, in the course of undergoing a transition from a ground state to an excited state thereof, said energy donor absorbs light.

16. The composition of claim 1, wherein, in the course of undergoing a transition from an excited state thereof, said energy donor emits radiation.

17. The composition of claim 1, wherein said energy acceptor is converted from said acceptor ground-state to said acceptor excited-state upon receiving energy from said energy donor.

* * * * *